US011285038B2

(12) United States Patent
Dijkstra et al.

(10) Patent No.: US 11,285,038 B2
(45) Date of Patent: Mar. 29, 2022

(54) MULTI-FUNCTION MASSAGE STONE

(71) Applicant: ShenZhen Kaiyan Medical Equipment Co, LTD, Shenzhen (CN)

(72) Inventors: Alain Dijkstra, Amstelveen (NL); Jonathan James Knight, Kent (GB); Jooeun Kim, Seoul (KR); Yong Zhang, Changde (CN)

(73) Assignee: ShenZhen Kaiyan Medical Equipment Co., LTD, Shenzhen (CN)

( * ) Notice: Subject to any disclaimer, the term of this patent is extended or adjusted under 35 U.S.C. 154(b) by 243 days.

(21) Appl. No.: 15/972,101

(22) Filed: May 4, 2018

(65) Prior Publication Data
US 2019/0336326 A1 Nov. 7, 2019

(51) Int. Cl.
A61F 7/00 (2006.01)
A61N 5/06 (2006.01)

(52) U.S. Cl.
CPC ............ A61F 7/007 (2013.01); A61N 5/0613 (2013.01); A61F 2007/0075 (2013.01); A61F 2007/0078 (2013.01); A61F 2007/0086 (2013.01); A61F 2007/0096 (2013.01); A61N 2005/0626 (2013.01); A61N 2005/0643 (2013.01);
(Continued)

(58) Field of Classification Search
CPC ...... A61N 5/00; A61N 5/0616; A61N 5/0613; A61N 2005/007; A61N 2005/0626; A61N 2005/0643; A61N 2005/0644; A61N 2005/0651; A61N 2005/0652; A61N 2005/0654; A61N 2005/0659; A61N 2005/0662; A61N 2005/0663; A61F 7/007; A61F 2007/0071; A61F 2007/0075;
(Continued)

(56) References Cited

U.S. PATENT DOCUMENTS 6,129,687 A * 10/2000 Powell .................. A61H 15/02
220/4.07
6,702,837 B2 * 3/2004 Gutwein .............. A61N 5/0616
606/9
(Continued)

FOREIGN PATENT DOCUMENTS

CA 2440783 A1 3/2004
CN 2738531 Y 11/2005

OTHER PUBLICATIONS https://squareup.com/store/meridian-energy-massage/item/electric-hot-stone-massager?square_lead=item_embed.
(Continued)

Primary Examiner — Timothy A Stanis
Assistant Examiner — Benjamin M. Kusiak
(74) Attorney, Agent, or Firm — Emanus, LLC; Willie Jacques

(57) ABSTRACT

A multi-function massage stone, for use in spas and massage facilities, includes a spherical body constructed of an upper portion and a lower portion which creates a hollow structure within the spherical body. The massage stone includes a user input device for regulating the hot or cold temperature of the massage stone, an LED assembly for providing light therapy, a heating and cooling device for providing hot and/or cold therapy, respectively, a controller device communicably coupled to the input device, and a battery located towards the inner side of the lower portion of the spherical body unit for providing power to the connected to the LED assembly, input device and controller device.

16 Claims, 6 Drawing Sheets

(52) U.S. Cl.
CPC ............ *A61N 2005/0651* (2013.01); *A61N 2005/0654* (2013.01); *A61N 2005/0659* (2013.01); *A61N 2005/0662* (2013.01); *A61N 2005/0663* (2013.01)

(58) Field of Classification Search
CPC ...... A61F 2007/0078; A61F 2007/0086–0088; A61F 2007/0096
USPC .......................................................... 601/15
See application file for complete search history.

(56) References Cited

U.S. PATENT DOCUMENTS

| | | | | |
|---|---|---|---|---|
| 8,715,210 | B2 * | 5/2014 | Orlando | A61H 7/003 601/15 |
| 9,895,285 | B2 * | 2/2018 | Ingrassia | A61H 39/04 |
| 9,962,309 | B2 * | 5/2018 | Connors | A61H 1/008 |
| 2007/0282400 | A1 * | 12/2007 | Gorham | A61B 18/04 607/88 |
| 2008/0053979 | A1 * | 3/2008 | Toya | A61F 7/007 219/201 |
| 2008/0188915 | A1 * | 8/2008 | Mills | A61F 7/007 607/112 |
| 2010/0010480 | A1 * | 1/2010 | Mehta | A61B 18/14 606/9 |
| 2011/0144546 | A1 * | 6/2011 | Crothers | A61H 7/003 601/15 |
| 2012/0109026 | A1 * | 5/2012 | McWilliams | A61H 37/00 601/17 |
| 2012/0109232 | A1 * | 5/2012 | Mohn | A61N 1/0456 607/3 |
| 2012/0165907 | A1 * | 6/2012 | Wagenaar Cacciola | A61N 5/0616 607/94 |
| 2014/0358204 | A1 * | 12/2014 | Dickie | A61F 7/007 607/109 |
| 2014/0378555 | A1 * | 12/2014 | Hung | A61N 1/30 514/773 |
| 2015/0174425 | A1 * | 6/2015 | Toyos | C12N 13/00 606/127 |
| 2015/0238349 | A1 * | 8/2015 | Giuliani | A61F 7/00 602/2 |
| 2015/0305923 | A1 * | 10/2015 | Ebel | A61F 7/00 601/15 |
| 2016/0175140 | A1 * | 6/2016 | Chen | A61F 7/02 607/101 |
| 2016/0242990 | A1 * | 8/2016 | Demski, Sr. | A61H 7/003 |
| 2016/0373564 | A1 * | 12/2016 | Motohashi | H04M 1/026 |
| 2018/0015299 | A1 * | 1/2018 | Kawa | A61N 5/0617 |
| 2018/0093121 | A1 * | 4/2018 | Matsuura | A63B 21/00845 |
| 2019/0274873 | A1 * | 9/2019 | Schoeggler | A61F 7/02 |

OTHER PUBLICATIONS

Meridian Energy Massage https://meridian-energy-massage.square.site/product/electric-hot-stone-massager/4?cs-true.
Sunpentown Rechargeable Portable Hand Warmer Black 5W SH-113FB https://www.target.com/p/sunpentown-rechargeable-portable-hand-warmer-black-5w-sh-113fb/-/A-50032510.
The Med-Stone http://www.themedstone.com/products.htm.

* cited by examiner

MULTI-FUNCTION MASSAGE STONE

FIELD OF DISCLOSURE

The present disclosure relates to a full-body massage tool, which can be used on the face, arm, leg and trunk such as for rubbing or pressing to promote blood circulation and increased metabolism, and thereby reduces fatigue and pressure. More specifically, the full-body massage stone is capable of providing hot and cold massage based on user requirement.

BACKGROUND

In general, a massaging stone device designed to relax your muscles uses a synthetic stone based on a natural massage stone to radiate heating or cooling massage effect to the body.

Full body massage to relax stiff muscles can help improve blood flow, relieve a mild headache, treat insomnia, depression, lack of sleep and lethargy, and provide psychological stability. In addition, massage can help the body excrete toxins, thereby reducing skin problems and improving physical function. In particular, massage has the ability to smooth flow of blood which helps to treat wrinkles, blemishes and acne, and also helps in improving skin color.

Whole-body massage is well known, and people generally understand the value of massages. As such, they are increasingly interested in massage devices, and the market has responded with various massage devices being developed and distributed.

In traditional cold stone massage therapies, natural stones are chilled in order to cool the stones. Then, appropriate pressure is applied to the skin and/or body using the stone for proper stimulation. However, during massage, friction, pressure, plus warm hands and body, reduce the effectiveness of cold stone massage thereby limiting the duration of the therapy. The classic way of cooling a stone necessarily results in a loss of its cooling properties and function over a short time. As a result, typical cold stone massage therapy has limited effectiveness, preventing the user from adequately benefiting from cold stone massage therapy. The disadvantage of these massage stone device is that they cannot be effectively treated according to the needs of stone therapy and therefore cannot effectively provide cold stone therapy.

In a traditional hot stone massage therapy, natural stones are heated, and then appropriate stone pressure is applied to the body by massage. Hot stone massage can be effective to improve body circulation and promote relaxation. However, traditional methods for heating the stone are not effective, and the stones will quickly lose their heat limiting the desired duration of the massage therapy. Rapid cooling of the hot massage stones results in loss of function in a short time. As a result, typical hot stone massage therapy has limited effectiveness, preventing the user from adequately benefiting from hot stone massage therapy. The disadvantage of these massage stones and other devices is that they cannot be effectively used according to the needs of stone massage therapy, and therefore cannot effectively treat the user.

However, massage stones tend to lose heat attained during the massage. A therapist conducting the stone massage therapy takes utmost care to ensure that the massage stones are a suitable temperature for use during therapy. Moreover, the therapists usually use a large number of massage stones to ensure successful use of the massage stones. A massage therapist must use care when using stones, in particular, use of a heating unit and cooling unit filled with hot water and cooled water may be impractical because the therapist is exposed to a burn risk and do not provide enough cooled effect. Many times, the stones are too hot, or not hot enough. Being too hot leads to wasted time for the user, as the therapist needs to use thongs or a large spoon, which is noisy and takes away from the relaxation of the session, so the therapist does not get burned. The therapist must cool the stones with cool water before they can be applied to the client's skin.

Other issues involved in stone massage therapy include: 1) therapist/client contact may be interrupted every time the therapist must stop to get new heated stones because the stones in use have lost their heat; slip and fall hazards due to the dripping of water on the floor; clean up and sanitizing the stones is very time consuming after a heated stone massage session especially if dealing with multiple heated stone sessions in a row.

In prior art, there are many electronic massage devices exist but none of them teach about providing a hot massage and a cold massage along with Light therapy effect by a single device. No prior art suggests or teaches the use of narrow therapeutic wavelength created by the light therapy unit such as LED device for providing light therapy on the user skin. Here are the examples:

US patent application publication US20160242990A1 by Justin Kiril et al. titled Heated Simulated Rock for Massage Therapeutic Use discloses a heating device to hold and heat the water that the current river rocks require in order to be heated, the device includes handheld portion and a lower portion to be heated. The upper, or handheld, portion is a hollow chamber which contains custom batteries, a three-position switch, a light emitting diode, a plug to recharge the batteries as needed, and the necessary wires to connect them all. Four wires from the upper, or handheld, portion of the rock will be connected to two resistors embedded in the lower portion to be heated to simulate a heated river stone when used on the back and limbs of a client.

Justin Kiril et. al teaches only a heating device, whereas the current invention teaches multifunction massage stone which provides a hot massage and a cold massage along with LED light therapy respectively. Justin Kiril et. al do not teach a device for providing cold effect and LED light therapy.

U.S. Pat. No. 8,715,210B2 by Dominic Orlando teaches A pocket-size self-heating massage stone includes a first receptacle having a rim portion, an interior recess and being made of ceramic slip, porcelain or stoneware slip and a second receptacle having a rim portion, an interior recess and being made of ceramic slip, porcelain or stoneware slip. A heating element is arranged in the interior recess of the second receptacle and being positioned in direct contact to transmit heat directly to a surface of the second receptacle such that the heating element only directly heats the second receptacle and does not directly heat the first receptacle. A rechargeable battery is disposed within the massage stone. The first and second receptacles are connected to one another via only the rim portions and the interior recesses of the first and second receptacles are free of connectors which connect together the first and second receptacles.

Dominic Orlando Only teaches a pocket-size self-heating massage stone that provide hot massage, whereas the current invention teaches a multifunction massage stone which provides multiple massage such as hot massage and cold massage along with LED light therapy. Dominic Orlando does not teach a device that provides a cold effect and LED light therapy. Further, Dominic Orlando does not teach about the use narrow therapeutic wavelength created by the light therapy unit such as LED device for providing light therapy on the user skin.

In order to overcome these limitations, there is a need for a massage device that enhances user convenience and improved hot, cold and LED therapy functions to promote muscle blood circulation and relaxation, not just physical stimulation of the skin.

Therefore, it is an object of the present invention to provides a multifunction massage stone device with heating, cooling and LED element uses in stone massage therapy.

It is further an object of the present invention to obviate the above and other disadvantages from existing art and to provide a multifunction massage stone device which is a lightweight, portable, safe, waterproof, user friendly, attractive and has a low production cost.

It is further an object of the present invention to provide a multifunction massage stone apparatus which may replace conventional method of massage stone therapy.

It is further an object of the present invention to provide a multifunction massage stone device capable of maintaining a temperature control, LED light intensity, and therapy time of the massage stones during a stone massage therapy.

SUMMARY OF THE DISCLOSURE

This disclosure is not limited to the particular systems, and methodologies described herein, as there can be multiple possible embodiments of the present disclosure which are not expressly illustrated in the present disclosure. The terminology used in the description is for the purpose of describing the particular versions and embodiments of the present invention, and is not intended to limit the scope of the present disclosure.

The present invention relates to a multifunction massage stone for providing hot and cold massage with LED light therapy on the biological surface such as skin. It is known in the prior art that separate hot massage stone device and LED therapy device are used to provide skin treatment and there is no such device present which provide cold stone massage in the same efficient manner. So, there is a need to have a single device which provides hot massage, cold massage and LED light therapy. The present invention discloses a multifunction device which act as hot massage stone to provide hot massage, cold massage stone to provide cold massage along with the LED light therapy based on user requirement.

Another consequence of the relative short life of the electronic component of the electronic massage device due to exposure to the environment conditions. The present multifunction massage stone is water resistant and higher durability to the environment conditions.

It is desirable to ensure that data stored in a flash memory system be reliable. The present invention discloses a method that marks existing data invalid only after new and valid data has been correctly written. As a result, the security of the data can be guaranteed The present invention is directed to a multi-function massage stone for use in spas, and massage facilities, and other health and beauty establishments. The massage stone, in a preferred embodiment, comprises a generally spherical-shaped body comprising an upper portion and a lower portion that when connected form a hollowed spherical-shaped body. Wherein the upper portion and the lower portion create a hollow structure within the spherical body upon attaching with each other. This formed hollow structure comprises an input device for receiving at least one input from a user; an LED assembly located near to the upper portion, wherein the LED assembly releases light with narrow therapeutic wavelength; a heating and cooling device for providing hot and cold therapy, respectively; a controller device communicably coupled to the input device; the heating and cooling device; and a battery unit LED assembly, In an aspect of the present disclosure, the heating device is a heating wire with a temperature diffusion glue to evenly distribute the heat and to ensure a stable local temperature.

In an aspect of the present disclosure, the cooling device is a Peltier thermoelectric semiconductor device.

In an aspect of the present disclosure, the multi-function massage stone is adapted to provide hot and cold therapy based on the input received from the user at the input device.

In an aspect of the present disclosure, the multifunction massage stone acts as a hot massage stone. The multifunction massage stone can be used to rub or press against the face, arm, leg and torso parts and any other biological surface, such as rubbing or pressing, to promote blood circulation and improve metabolism, thereby relieving fatigue and stress. The multifunction massage stone could be made of a high strength, corrosion and water resistant material such as alumina, sapphire, ruby or any other suitable material. Further, the multifunction massage stone has excellent hardness, strength, chemical stability, high electrical insulation properties and high thermal conductivity.

In an aspect of the present disclosure, the multifunction massage stone acts as a cold massage stone. The multifunction massage stone when used as a cold stone massage with Oriental Medicine for relief from swelling, muscle cramps, headache, pain relief, stiffness, bruises and so on. Cold stone massage promotes lymphatic and blood circulation, shrinks blood vessels and stimulates the parasympathetic nervous system. As a result, the multifunction massage stone acting as a cold stone massage increases muscle activity while reducing muscle spasms, muscle aches, muscle inflammation and swelling. When used with skin care products, cold stone massage can sooth the skin, improve elasticity and tighten pores.

The foregoing has outlined rather broadly the features and technical advantages of the present invention in order that the detailed description of the invention that follows may be better understood. Additional features and advantages of embodiments of the invention will be described hereinafter which form the subject of the claims of the invention. The conception and specific embodiment disclosed herein may be readily utilized as a basis for modifying or designing other structures for carrying out the same or similar purposes of the present invention. Please note that such equivalent constructions do not depart from the scope of the invention as set forth in the appended claims. The novel features which are characteristic of the invention, both as to its organization and method of operation, together with further objects and advantages, will be better understood from the following description when considered in connection with the accompanying figures. Each of the figures is provided for the purpose of illustration and description only and is not intended as a limitation of the scope of the present invention or appended claims.

BRIEF DESCRIPTION OF THE DRAWINGS

For a complete understanding of the present invention, reference is now made to the aforementioned and following descriptions taken in conjunction with the accompanying drawing, in which.

Like numerals refer to like elements throughout the present disclosure.

DETAILED DESCRIPTION OF THE INVENTION

Embodiments of the present disclosure will be described more fully hereinafter with reference to the accompanying drawings in which like numerals represent like elements throughout the several figures, and in which example embodiments are shown. Embodiments of the claims may, however, be embodied in many different forms and should not be construed as limited to the embodiments set forth herein. The examples set forth herein are non-limiting examples and are merely examples of other possible examples.

To achieve the above-described features and advantages, the present disclosure is directed to a multi-function massage stone for use in the spa and massage. The massage stone comprises a spherical body comprising an upper portion and a lower portion, wherein the upper portion and the lower portion create a hollow structure within the spherical body upon attaching with each other. The hollow structure comprises an input device for receiving at least one input from a user, an LED assembly located towards the front end of the inner side of the upper portion, wherein the LED assembly releases light with narrow therapeutic wavelength, a heating and cooling device for providing hot and cold therapy respectively, a controller device communicably coupled to the input device, the heating and cooling device for regulating temperature of the massage stone based on at least one input received from the user and a power source such as a battery unit connected to the LED assembly, input device and the controller device located towards the inner side of the lower portion of the spherical body.

Figure 1:
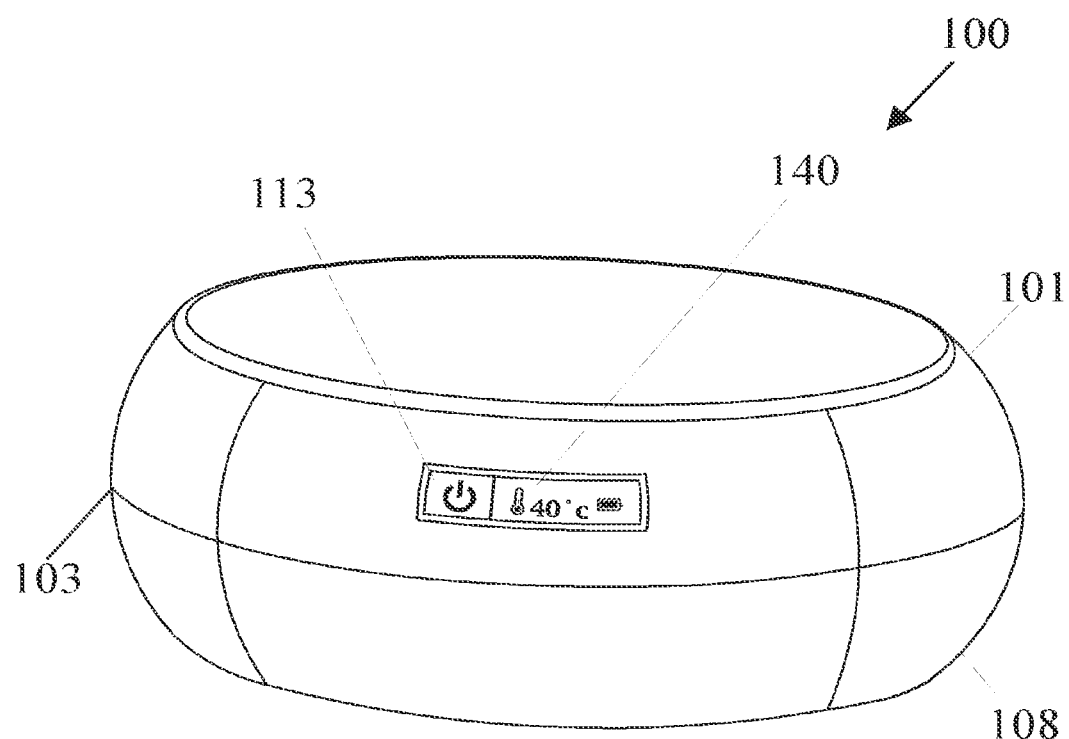
FIG. 1 illustrates a perspective view of a multi-function massage stone when upper and lower portion are adjoined together, according to various embodiments of the present disclosure.

FIG. 1 of the accompanying drawings, shows a perspective view of a closed multi-function massage stone 100. According to an embodiment, the multi-function massage stone 100 includes an upper portion 101 and a lower portion 108. The upper portion 101 includes an transparent panel made of Poly(methyl (methacrylate) (PMMA) or slice based glass (e.g thermoplastics, acrylic, Crylux, Plexiglas, Acrylite, Lucite, and Perspex sheet or panel) and any other suitable material for providing high transmittance and optical power.

The lower portion 108 is generally comprised of a ceramic (e.g., alumina, sapphire, ruby, etc.) or similar materials exhibiting, at a minimum, thermal stability, corrosion resistance, wear and water resistance. Materials of this sort, such as Alumina is used to form a transparent external structure for the multi-function massage stone 100 and allows the emittance of a large amount of far-infrared rays. In FIG. 1, there is shown a connecting part 103 which depicts the joining between the upper portion 101 and the lower portion 108 of the multi-function massage stone 100. The upper portion 101 and the lower portion 108 create a hollow structure when combined together at the connecting part 103. The various components provided in the hollow structure shall be explained in later part of the description.

In one embodiment, the properties of alumina which used in the lower portion 108 of the multifunction massage stone to provide additional health benefits to the user. The alumina are known to be effective in relieving stress by eliminating toxins and wastes from the body and form powerful energies through the high-infrared interaction of basalts. Alumina has also proven effective in lipolysis, immune enhancement, constitutional improvement, fatigue recovery, cell regeneration and activation, anti-aging, natural body repair and metabolic enhancement. Far-infrared has a positive effect on the flow of energy in the body. Alumina also increases the natural healing power of the body, increases the skin's ability to regenerate, increases collagen tissue activity in the body, and enhances elasticity. It also has the effect of improving the condition of the skin, hair and nails.

Further, the upper portion 101 may be made of the crystalline phase that is $\alpha$-Al2O3, having a density of 3.98 g/cm3 or more, linear transmittance of 90% to 95% or more, dielectric constant greater than 9.8, dielectric loss tangent is less than $2.5 \times 10^{-4}$ (1GC), flexural strength greater than 350~380 MPa. breakdown strength of 6.0~6.4 kV with thermal expansion coefficient $(6.5~8.5) \times 10^{-6}/°$ C. thereby providing high temperature alkali metal vapor with good corrosion. The raw material is Al2O3 with the purity of more than 99.99%, adding a trace of pure magnesia, lanthanum oxide, or yttria and other additives, adopting a continuous isostatic pressing process, atmosphere sintering or hot-pressing sintering to strictly control the grain size, get high-density transparent ceramic. The lower portion 108 is made up of Alumina as described above. In a preferred embodiment, the use of Al2O3 material makes the massage stone more portable and also provides higher material stability, high strength and 2 meters' free fall without damage.

Figure 2:
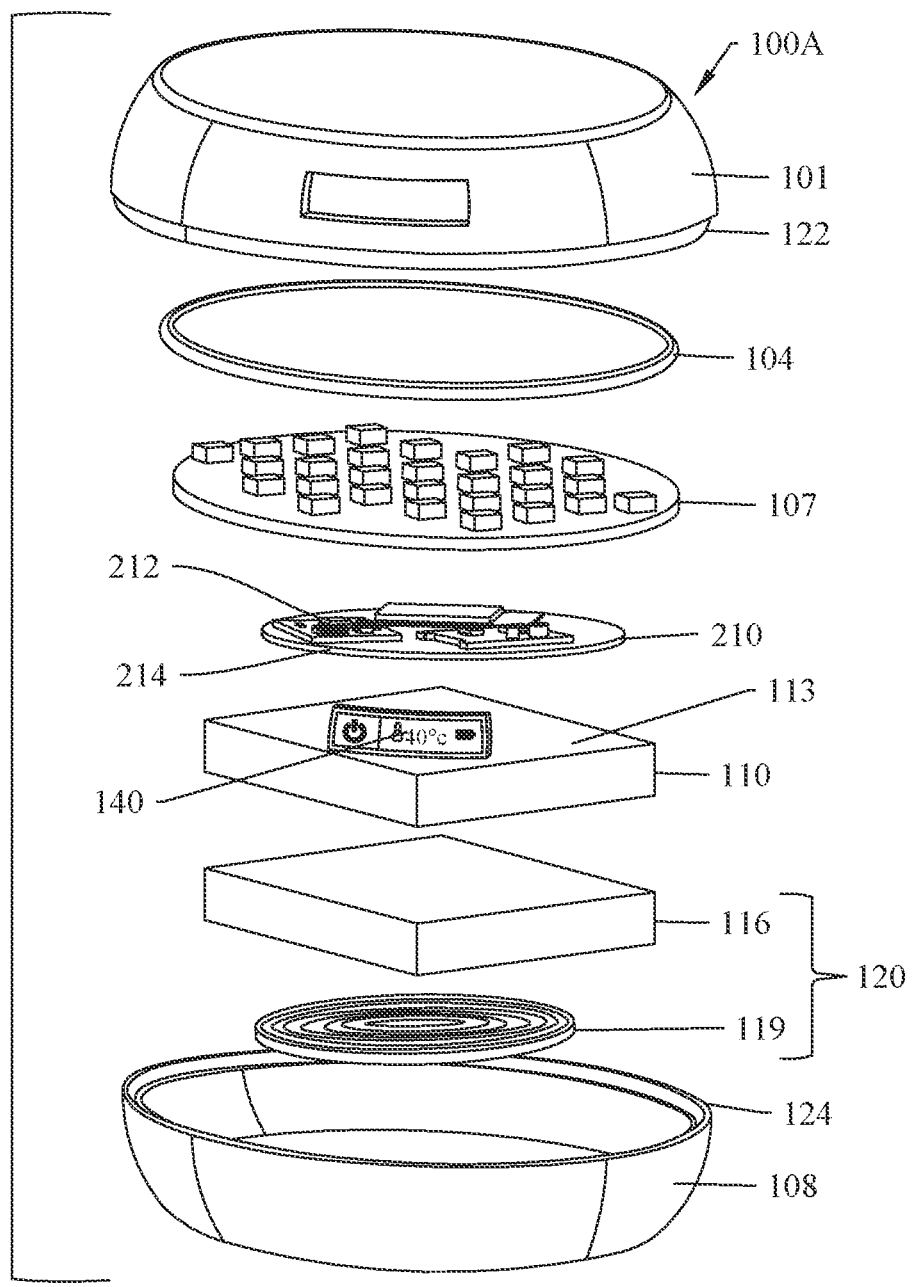
FIG. 2 illustrates an exploded perspective view of the multi-function massage stone according to various embodiments of the present disclosure.

As show in FIG. 2, In one embodiment, The Multifunction massage stone 100A can be a stand-alone cold massage stone which is adapted to provide cold stone massage on the user skin in a self-operable manner or via a massage therapist.

Figure 3:
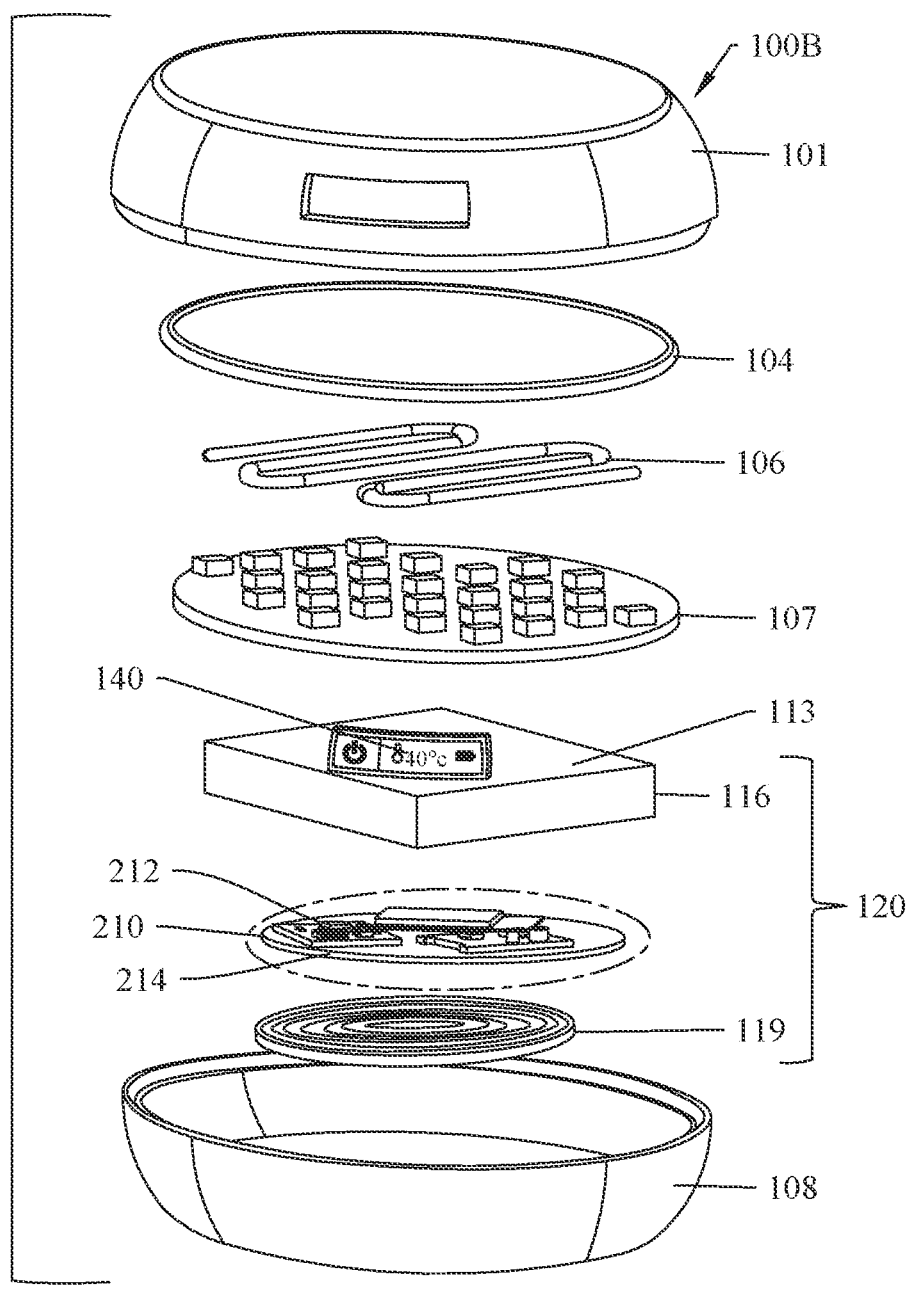
FIG. 3 illustrates an exploded perspective view of the multi-function massage stone according to various embodiments of the present disclosure.

As show in FIG. 3, In one embodiment, The Multifunction massage stone 100B can be a stand-alone hot massage stone which is adapted to provide hot stone massage on the user skin in a self-operable manner or via a massage therapist.

Figure 4:
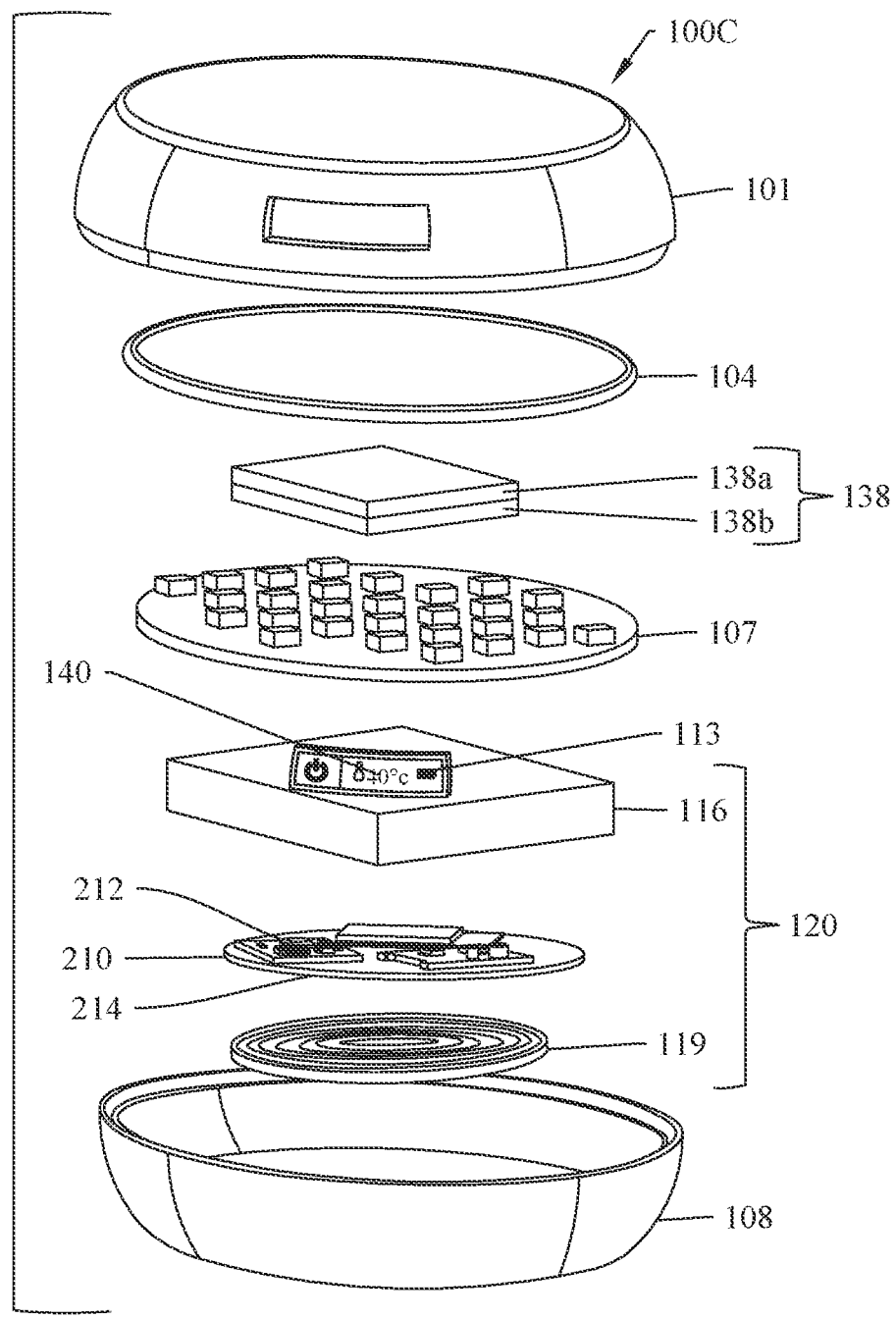
FIG. 4 illustrates an exploded perspective view of the multi-function massage stone according to various embodiments of the present disclosure.

As shown in FIG. 4, In one embodiment, The multifunction massage stone 100C can be a multifunction massage stone which is adapted to provide hot and cold stone massage on the user skin based on user input in a self-operable manner or via a massage therapist.

FIGS. 2, 3 & 4 of the drawings shows a multifunction massage stone 100A, 100B and 100C, respectively, in open/exploded views depicting the inner components. The inner components of a massage stone 100A (configured to act as standalone cold massage stone by disabling the heating element) includes a high-density ring 104, an LED assembly part 107, an input device 113, a cooling device 110, a controller device 210, and the battery unit 120.

In one embodiment, the inner components of the multi-function massage stone 100B (configured to act as stand-alone hot massage stone by disabling cooling element) includes the high-density ring 104, a heating device 106, the LED assembly part 107, the input device 113, the controller device 210, and the battery unit 120.

In one embodiment, the inner components of the multi-function massage stone 100C includes the high-density ring 104, the heating device 106, the LED assembly part 107, the input device 113, the cooling device 110, the controller device 210, and the battery unit 120. FIG. 2 shows an upper portion 101 which represents the upper hemispherical portion of the multi-function massage stone 100. There is a lower portion 108 which represents the lower hemispherical portion of the massage stone.

In one embodiment, the lower portion 108 (i.e., the lower hemispherical portion of the massage stone) may include a handle (not shown) for easy handling of the massage stone 100, and for providing more efficient massage to a user.

In the said FIGS. 2 & 3, the high-density ring 104 is capable of isolating the moisture content and is easy to clean. The high-density ring 104 is provided in a first connecting part 122 of the upper portion 101 which is adapted to be inserted in a second connecting part 124 of the lower portion 108 of the spherical body. The high-density ring 104 fits snugly over the first connecting part and thereby creates a waterproof seal, so that the multifunction massage stone 100 can be used under various conditions such as underwater, during the shower, along with pain relief creams or oils, etc.

In an embodiment, part 107 represents LED assembly which includes 880 nm medical-grade LED lamps and 660 nm medical-grade LED lamps, with FM function, according to the need for 50-400 HZ FM. The LEDs lamp assembly 107 transmit light energy to body tissues and joints, helping to relax the muscles and temporarily relieve minor pains such as those associated with arthritis. This device is used for massage regardless of the area of the body. The continual use of such pads for a certain period of time, usually 15-30 days, will help the user see a noticeable improvement to painful muscles or joints. Infrared and red LED lights deliver visible and invisible (IR) light energy to body tissues and joints, stimulating blood circulation and tissue healing areas. This is a natural and non-invasive treatment for those suffering from such pain.

The LED lamp assembly 107 in the massage stone 100, in an embodiment, uses light with a narrow therapeutic wavelength. They have no adverse side effects and no harmful rays. It also relieves muscle spasms, promotes circulation, and promotes wound healing.

In an embodiment, the multifunction massage stone 100 comprises an input device 113 for receiving an input from a user. The said input device 113 may be a push button, touch button, voice activated button or a combination thereof. The input device 113 is adapted to receive the user input in the form of at least one physical push, voice, gesture, or electronic signal from a computing device. The input device acts as an On/Off button switch which is located on the body multi-function massage stone. The input device is perfectly fitted between the upper portion 101 and lower portion 108 of the multi-function massage stone.

In an embodiment, the user input 113 includes at least one of a request of cold massage; a request of hot massage; selection of temperature range, but not limited to the selection of wavelength output from the LED assembly; wireless charging of the battery, or combinations thereof.

The input device 113 comprises a communication interface for communicating with other computing devices via near field communication means such as Bluetooth, NFC, Zigbee, infrared, and the like. The other computing device may be a smartphone, smartwatch, laptop, computer, processor enabled devices which are able to communicate via wired or wireless means or a combination thereof.

The input device 113 includes a display unit 140 which displays at least one notification to the user. The at least one notification may relate to various information useful to a user of a multi-function massage stone, such as real-time/temperature information of the multifunction massage stone, the surrounding temperature, battery information, hot or cold operation mode, technical error, battery replacement alert, system failure alert, device maintenance alert, hot massage information, cold massage information or a combination thereof.

In one embodiment shown in FIG. 4, when the multifunction massage stone device 100 is configured to act as a combination hot and cold massage stone device 100C which comprises a Peltier semiconductor device 138 (with a hot side 138a and a cold side 138b) that provides cooling to the massage stone. The cold side 138b acts as self-cooling equipment which is adapted to quickly reduce the temperature, and quickly achieve temperatures necessary for cold treatment. Each massage stone can hold a temperature of −3° C. for 60 minutes. The minimum temperature does not exceed −10° C.

In one embodiment, the Peltier semiconductor device 138 is small in volume as compared with a cooling method using a compressor and can be installed in a small space because of its light weight. The Peltier semiconductor device 138 can be simply changed to the polarity of the applied voltage to cool or heat it as appropriate for the application. The Peltier semiconductor device 138 includes a temperature controller. It includes accurate temperature control of ±0.1 degrees with temperature controller (not shown). The cooling device 110 includes thermoelectric elements such as a temperature controller, and a temperature sensor (not shown). The thermoelectric elements (not shown) without mechanical movement have a long lifespan. Additionally, there is no mechanical noise. The Peltier semiconductor device 138 can cool a specific part without unnecessarily cooling the entire system. Therefore, the stone massage device with Peltier semiconductor device 138 (the cold side 138b) is capable of achieving the best efficiency with minimal energy.

In an advantageous embodiment, the cold massage stone 100A is effective in promoting lymph and blood circulation, shrink blood vessels, and stimulate the parasympathetic nervous system. As a result, muscle vitality, muscle spasms, myalgia, muscle inflammation and edema are reduced. Cold stones pressure blood vessels to stimulate the nervous system and spill toxins and cysts out of the body. The massage stone cools down between to −1 and −3 degrees Celsius.

In an advantageous embodiment, the Cold massage stone device 100A having the LED assembly provide a LED and cold massage therapy to reduce inflammation in immediate painful areas. When using cold stone 100A on a wound, the blood circulation is initially slowed down, and later a large amount of new blood is supplied to the site, so that natural healing is promoted. Cold stone therapy is also effective for severe edema, swelling eyes, acne, pregnancy and leg massage. The temperature of the stone is below body temperature (36 degrees).

In an advantageous embodiment, the Cold massage stone device 100A having the LED assembly provide a LED and cold massage therapy which is used for skin care, obesity and cellulite management, muscle tissue tension and stiffness, and pain relief. In particular, deep tissue chair massage effectively relieves the pain of muscles, fascia and ligaments. This massage can find painful sites and use stones to dive deeper into the muscles.

In an advantageous embodiment, the cold massage stone device 100A having the LED assembly provide a LED therapy and cold massage therapy simultaneously which helps to promote lymphatic and blood circulation throughout the body. When Cold massage and LED therapy applied simultaneously at the desired site or area or a user body via cold stone massage device 100A, the therapy can improve blood coagulation and analgesia, edema and severe shoulder pain, and reduce white blood cells, so the user can feel relief from inflammation. It also helps relieve fatigue, reduce pain and heal injuries. Cold stone therapy increases blood pressure and heart rate by overcoming peripheral blood circulation, improved metabolism, reduced edema, reduced pain, increased volume, increased muscle tone. The cold stone massage device 100A also provides a cryotherapy (cold therapy) relieves muscle and joint inflammation by relieving radiation and swelling at painful sites. In addition, it can effectively control obesity by eliminating body waste, promoting digestion and metabolism, and increasing nutrient supply to cells.

In one embodiment, when the multifunction massage stone device 100 configured to act as a hot massage stone device 110B which provides a hot massage and LED light therapy which is helpful for rhinitis and other sports injuries. Further, in one embodiment, the hot massage and LED therapy provided by the hot stone massage device 100B on the user desired body part, The hot massage and LED therapy helps user to relax and relieve muscle cramps and soreness, relieve pain associated with joint pain and arthritis, relieve arthritis-related stiffness, relieves the affected tissues around joints or areas, and help to increase blood flow circulation, to help the body's natural healing process on the user desired body part where the therapy is applied.

In another embodiment, when the multifunction massage stone configured to act as 100B is used as a hot massage stone 100B as shown in FIG. 3, there is shown a heating device 106 which warms up inner portion of the spherical body of massage stone 100 and transfer the heat to the outer surface of the spherical body of massage stone, thereby provides a hot therapy on the user desired body part or area. The heating device 106 is a heating wire with a temperature diffusion glue to evenly distribute the heat and ensure a stable local temperature. The heating device generates a temperature range from 50 degrees Celsius and 60 degrees Celsius for providing hot therapy. The heating device 106 may include a temperature controller (not shown) and temperature sensors which helps the heating device 106 to warm up the massage stone 100B at user desired temperature or at a default temperature.

In another embodiment, when the multifunction massage stone configured to act as a hot massage stone 100B as shown in FIG. 3. The hot massage stone 100B provide hot massage and LED light therapy simultaneously which result in in-depth detoxification and deep relaxation on the user body part, where the therapy applied by the user or received by the user though a massage therapist. The hot massage stone 100B device is combined with LED light transmitted through the LED assembly via transparent upper portion 101 of the spherical body of the multifunction massage stone 100B to stimulate and relax the circulatory system of the body part. This circulation helps muscles release toxins and promote natural healing. In addition, hot stone massage with LED therapy can penetrate deep into sore muscles, helping to helping to ease muscle pain. Pain and muscle spasms are eliminating, providing the recipient with a feeling of physical and mental well-being. This combined effect contributes to an enhanced state of relaxation, relieving stress and laying the foundation for the recovery and rejuvenation of the body, mind and spirit.

In one embodiment, when the multifunction configured to act as hot massage stones device 100B is used to provide massage involving the application of hot stones (hyperthermia) to the body in the context of therapeutic massages. The sleek, smooth massage tone is warmed to a comfortable temperature and can include essential oils and palm massage. Through the introduction of heat, such massage promotes deep relaxation, improved detoxification, reduced muscle tension, stress and fatigue. Body treatment devices utilizing the combination of LED light and heat penetration during massage help to improve the treatment effect.

In an advantageous embodiment, the heat generated by the hot massage stones promotes blood circulation, contributes to the relief of chronic pain and improves muscle relaxation. Combining LED light therapy and hot massage stone therapy provides a much more effective treatment for fibromyalgia, arthritis, carpal tunnel syndrome, musculoskeletal issues and muscle cramps.

In an embodiment of the present disclosure, there is provided a controller device (210) which is communicably coupled to the input device 113, the heating 106 and cooling device 110 or regulating temperature of the massage stone based on at least one input received from the user. The controller device 210 is configured to control the operation of the massage stone while being operated by a user. The controller device 210 is further adapted to maintain the temperature of the massage stone on the basis of input by a user at the user input device.

Figure 3A:
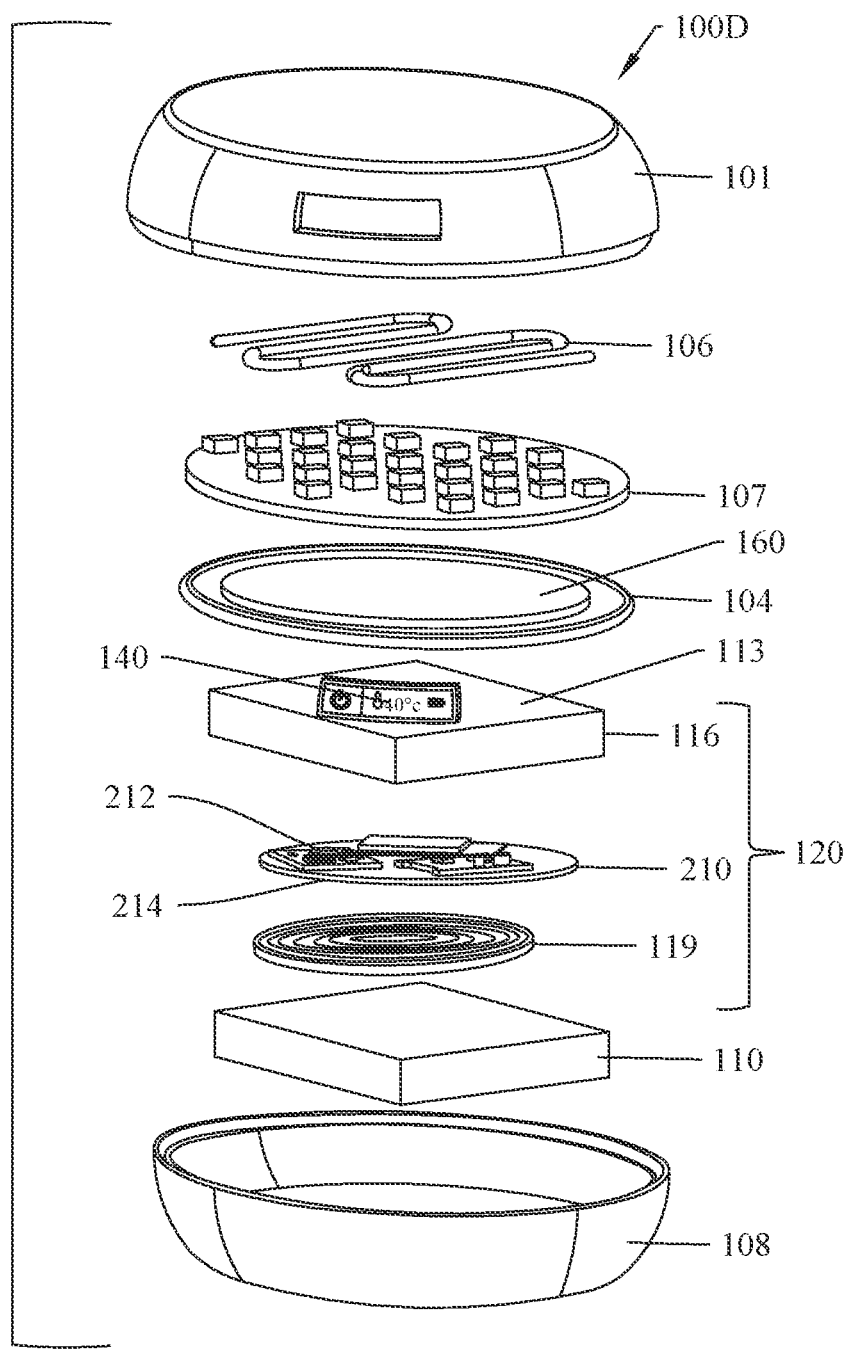
FIG. 3A illustrates an exploded perspective view of the multi-function massage stone according to various alternate embodiments of the present disclosure.

In an embodiment illustrated in FIG. 3A, the multipurpose massage stone 100 acts as a simultaneous hot and cold therapy massage stone 100D, where, the upper portion 101 and the lower portion 108 are configured to provide hot stone and cold stone therapy respectively. An insulating layer 160 can be used across the connecting part joining the upper portion 101 and lower portion 108. The insulating layer 160 enables the user to use the massage stone 100D both in hot and cold modes simultaneously.

In an advantageous embodiment, the multifunction massage stone 100 effectively manage pain and disease of the user's body by transmitting the cold and hot therapy or massage effectively to the body and outputting near-infrared and visible light LEDs. In addition, thermostats maintain the treatment temperature for 60 minutes, while Peltier devices make temperature control very sensitive. A timer allows the user to set the therapy duration.

Figure 5:
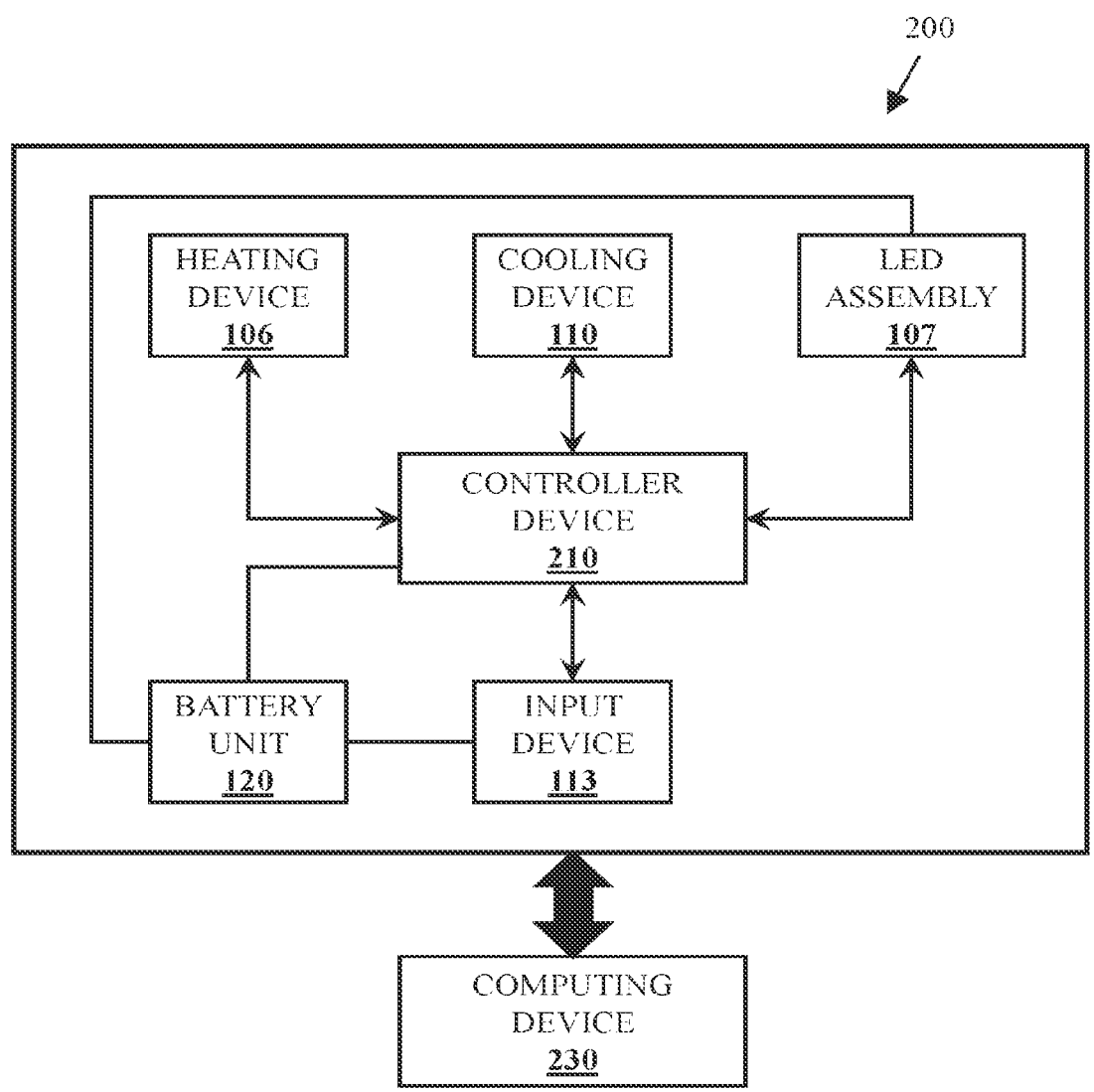
FIG. 5 is a block diagram illustrating the function of the massage stone, according to various embodiments of the present disclosure.

Referring to FIG. 5 of the enclosed drawings, there is shown a block diagram 200 illustrating the various components of the massage stone described above. There is shown an input device 113 which is coupled to the LED assembly 107, the controller device 210, the heating device 106, the cooling device 110, and the battery unit 120. There is also shown a computing device 230 which is operated by a user. The controller device 210 includes a microcontroller or microprocessor and a memory. All the above mentioned component are connected to each other.

FIG. 5, there is provided the battery unit 120 which includes a rechargeable battery 116 and a wireless charging module 119, wherein the rechargeable battery 116 connected to the LED assembly 107, the input device 113 and the controller device 210 for providing electrical power while operating the massage stone when in operating mode. The battery unit 120 includes the wireless charging module 119 with a non-contact charging module 212 and a main chip 214 for charging the rechargeable battery 116 wirelessly. Such batteries have long lasting power.

In an embodiment, the input device 113 is adapted to establish a communication with at least one computing device 230 via near field communication. The computing device may include a user interface which allows user to send input to the input device 113. The user can select an input via the user interface (not shown) such as hot massage, cold massage, desired temperature, time duration of hot and cold massage and others and send a command or input to the input device 113 using the computing device 230. The said computing device 230 can be coupled to the massage stone with the help of near field communication interface. The computing device is selected from a group of smartphone, smartwatch, laptop, computer, processor enable computing devices and combination thereof.

In an embodiment, if the input device 113 receives a request for cold massage from the user computing device via wireless means such as near field communication, the multifunction massage stone 100 will act as cold massage stone 100B. The input device 113 transmits the cold massage request signal to the controller 210. Upon receiving the cold massage request signal, the controller device 210 is adapted to activate the cooling device 110. The LED assembly is used for providing a narrow therapeutic wavelength and light energy. Upon activation, the cooling device 110 acts as a self-cooling unit which is adapted to quickly reduce the local temperature within hollow structure of the multifunction massage stone 100 and cool down inner portion of the upper portion 101 and lower portion 108, wherein the outer portion of the upper portion 101 and lower portion 108 also gets cool down below zero-degree Celsius (0° C.) or a desired temperature level and quickly achieve the effect of cold treatment. The upper portion 101 and lower portion 108 portion is made up of high thermal conductivity material, so that the cooling is transferred from inner surface to outer surface of the multifunction massage stone 100 very quickly. Therefore, the user can massage the desired body part with the cooled outer portion along with the LED emitted light energy.

In an embodiment, if the input device 113 receives a request for hot stone massage from the user computing device via wireless means such as near field communication, the multifunction massage stone 100 will act as a hot massage stone 100. The input device 113 transmits the hot massage request signal to the controller device 210. Upon receiving the hot massage request signal, the controller device 210 is adapted to activate the heating device 106 and the LED assembly for providing heating effect and a narrow therapeutic wavelength with the light energy. Upon activation, the heating device 106 which includes a heating wire with a temperature diffusion glue to make the heat evenly distributed to ensure a stable local temperature. The heating device 106 generates a temperature range between 50 degrees Celsius and 60 degrees Celsius for providing hot therapy. The heating device 106 will heat up or increase the temperature of inner portion of the lower portion 108 and upper portion 101, wherein the outer portion of the lower portion 108 and upper portion 101 will also heat to a desired temperature level and quickly achieve the effect of heat treatment. The lower and upper hemispherical portion which are made up of high thermal conductivity material, so that the heat is transferred from inner surface to outer surface of the multifunction massage stone very quickly. Then the user can massage desired body part with the heated or warmed outer portion along with the LED emitted light energy.

The LED assembly 107 as described herein above, are 80 nm medical-grade LED lamps and 660 nm medical-grade LED lamps, with FM function, according to the need for 50-400 Hz FM. The massage stone is adapted to provide LED therapy in combination to the hot or cold therapy in a selective manner.

In one embodiment, the controller device 210 is configured to control the operation of the massage stone and maintaining the temperature of the multifunction massage stone on the basis of input from the user as received at the input device 113. The controller device 210 is adapted to configure the multifunction massage stone as a hot massage stone 100B by disabling the cooling device based on the hot massage request received from the input device 113 from the user. Further, in another embodiment, the controller device 210 is adapted to configure the multifunction massage stone as a cold massage stone 100A by disabling the heating device based on the hot massage request received from the input device 113 from the user.

In FIG. 4, there is shown the combination hot and cold massage stone device 100C, which provide hot/cold therapy to users based on the user input.

In an embodiment, the heating device 106 relates to the heating device 106 which may include a heating wire, the temperature controller (not shown) and a temperature sensor (not shown) for providing hot stone therapy to the user.

In another embodiment, the cooling device relates to a cold side 138b of the Peltier semiconductor device 138 which may include temperature controller (not shown) and temperature sensors (not shown) for providing cold stone therapy to the user.

In one embodiment, the heating device 106 and the cooling device 110 connected to a common temperature controller (not shown) and temperature sensors (not shown) provided in the multifunction massage stone 100.

In an alternate embodiment, the heating device 106 (i.e. including heating wire) is arranged in such a way that it will not obstruct the light coming from the LED assembly 107. Wherein, the LED array present in the LED assembly 107 is arranged in such a way that it will correspond to the hollow areas of the heating wire.

In an alternate embodiment, the cooling device 110 is arranged in such a way that it will not obstruct the light coming from the LED assembly 107.

The battery unit 120 is adapted to provide power supply to the massage stone when in operating mode. The battery unit 120 includes the wireless charging module 119 with the non-contact charging module 212 and the main chip 214 for charging the rechargeable battery 116 wirelessly. Such batteries have long lasting power.

The present disclosure has many advantages. According to the present disclosure, the effect of each therapy can be maximized by combining ordinary massage functions with stone massage therapy and LED therapy, thereby enabling the user to perform the therapy easily and effectively. Therefore, according to the preference of the user, the treatment can be applied to various parts of the body, and the functions of the massage device and the massage stone are combined.

The term "multifunction massage stone", "hot massage stone", "cold massage stone" refer to a massage device which is adapted to provide hot and cold massage therapy along with LED light therapy based on the user input. The massage stone can act as "multifunction massage stone", "hot massage stone", "cold massage stone" and the combination thereof.

The term "user" and "therapist" refer to a person who is using or applying the multifunction massage stone for providing hot and cold massage along with light therapy on the skin of the therapy recipient.

The terms "a," "an," "the" and similar referents used in the context of describing the invention (especially in the context of the following claims) are to be construed to cover both the singular and the plural unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

It is contemplated that numerical values, as well as other values that are recited herein, are modified by the term "about", whether expressly stated or inherently derived by the discussion of the present disclosure. As used herein, the term "about" defines the numerical boundaries of the modified values so as to include, but not be limited to, tolerances and values up to, and including the numerical value so modified. That is, numerical values can include the actual value that is expressly stated, as well as other values that are, or can be, the decimal, fractional, or another multiple of the actual value indicated, and/or described in the disclosure.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markup groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Although specific embodiments and certain structural arrangements have been illustrated and described herein, it will be clear to those skilled in the art that various other modifications and embodiments may be made incorporating the spirit and scope of the underlying inventive concepts and that the same is not limited to the particular methods and structure herein shown and described except in so far as determined by the scope of the appended claims.

LISTING OF COMPONENTS

100 Multifunction massage stone
101 Upper Portion of the spherical body
103 Connecting Part
104 High density Ring
106 Heating Device
107 LED assembly Part
108 Lower Portion
110 Cooling Device
210 Controller Device
113 Input Device
116 Rechargeable Battery
119 Wireless Charging Unit
124 Second Connecting Part
122 First Connecting Part
230 Computing Device

NOT LABELED COMPONENTS

Non-Contact Charging Module
Main Chip
Display Unit
User Interface
Temperature Sensor
Temperature Controller

What is claimed is:

1. A multi-function massage stone for use in spa and massage facilities, the massage stone comprising:
   a spherical body comprising an upper portion and a lower portion,
      wherein the upper portion and the lower portion create a hollow structure within the spherical body upon attaching with each other, the hollow structure comprising:
      an input device for receiving at least one input from a user,
      an LED assembly, located between the input device and the upper portion,
      wherein the LED assembly is capable of delivering radiation in forms of visible and Infrared (IR) light energy,
      wherein the upper portion is constructed of a transparent material configured for allowing the radiation from the LED assembly to pass through the transparent material, in order to provide transmittance and optical power,
      wherein the transparent material of the upper portion is crystalline phase Alumina,
      a heating device and a cooling device configured for providing hot and cold therapies, respectively,
      an insulating layer across a connecting part joining the lower portion and the upper portion,
      wherein the insulating layer enables the user to use the massage stone both in hot and cold modes simultaneously,
      a controller device communicably coupled to the input device, and
      a battery unit connected to the LED assembly, the input device, the heating device, the cooling device, and the controller device.

2. The multi-function massage stone of claim 1, wherein the LED assembly comprises an LED device for irradiating visible light energy having wavelengths of 660 nm and 880 nm.

3. The multi-function massage stone of claim 1, wherein the LED assembly comprises a FM module for using 50-400 Hz.

4. The multi-function massage stone of claim 1, wherein the lower portion is constructed of Alumina.

5. The multi-function massage stone of claim 1, wherein the hollow structure comprises;
the upper portion comprising a first connecting part which is adapted to be inserted into a second connecting part of the lower portion of the spherical body,
wherein the spherical body includes a ring element snugly fit over the first connecting part and thereby creating a waterproof sealing.

6. The multi-function massage stone of claim 1, wherein the heating and cooling device is a Peltier thermoelectric semiconductor device.

7. The multi-function massage stone of claim 1, wherein the heating and cooling device is a heating wire with a temperature diffusion glue to evenly distribute the heat.

8. The multifunction massage stone of claim 1, wherein the heating device is configured for generating a temperature range from 50 degrees Celsius to 60 degrees Celsius for providing the hot therapy.

9. The multi-function massage stone of claim 1, wherein the input device comprises at least a push button, a touch button, a voice activated button or combinations thereof.

10. The multi-function massage stone of claim 1, wherein the user input includes a request of cold massage, a request of hot massage, selection of temperature range, selection of wavelength output from the LED assembly, wireless charging of battery and combinations thereof.

11. The multi-function massage stone of claim 1, wherein the input device is adapted to receive the user input in the form of at least one of a physical push, voice, gesture, or electronic signal from a computing device.

12. The multi-function massage stone of claim 1, wherein the input device further comprises a communication interface for communicating with other computing devices via near field communication.

13. The multi-function massage stone of claim 12, wherein the input device includes a display unit which displays at least one notification.

14. The multi-function massage stone of claim 13, wherein the at least one notification includes real time temperature information of the multi-function massage stone, battery information, hot massage information, cold massage information and combinations thereof.

15. The multi-function massage stone of claim 1, wherein the multi-function massage stone is adapted to be used on the body of the user.

16. The multi-function massage stone of claim 1, wherein the battery unit includes a non-contact wireless charging module and a main chip configured for charging the rechargeable battery wirelessly.

* * * * *